(12) United States Patent
Johnson et al.

(10) Patent No.: US 6,224,027 B1
(45) Date of Patent: May 1, 2001

(54) TELESCOPING FLEXIBLE OXYGEN SUPPLY TUBE SUPPORT STAND

(76) Inventors: Lynn D. Johnson; Dean L. Johnson, both of 7141 Bramlett La., Harrison, TN (US) 37341

( * ) Notice: Subject to any disclaimer, the term of this patent is extended or adjusted under 35 U.S.C. 154(b) by 0 days.

(21) Appl. No.: 09/461,880

(22) Filed: Dec. 15, 1999

(51) Int. Cl.[7] ........................................... A47F 5/00
(52) U.S. Cl. ........................ 248/125.8; 248/129
(58) Field of Search .............. 248/125.8, 129, 248/125.9, 132, 161, 157

(56) References Cited

U.S. PATENT DOCUMENTS

| | | |
|---|---|---|
| 4,480,639 | 11/1984 | Peterson et al. . |
| 4,593,688 | 6/1986 | Payton . |
| 4,654,026 | 3/1987 | Underwood . |
| 4,739,757 | 4/1988 | Edwards . |
| 5,236,160 * | 8/1993 | Sechelski .................... 248/125.1 |
| 5,355,876 | 10/1994 | Brodsky et al. . |
| 5,392,808 | 2/1995 | Pierce . |
| 5,421,548 * | 6/1995 | Bennett et al. .................. 248/129 |
| 5,470,037 * | 11/1995 | Willis ........................... 248/125.9 |
| 5,645,048 | 7/1997 | Brodsky et al. . |
| 5,752,511 | 5/1998 | Simmons et al. . |
| 5,772,162 * | 6/1998 | Lin ........................... 248/125.1 X |

* cited by examiner

Primary Examiner—Ramon O. Ramirez
(74) Attorney, Agent, or Firm—John D. Gugliotta

(57) ABSTRACT

The invention is a apparatus and method for holding the oxygen hose above a patient's head. It also flexes whenever the patient turns in bed. The device is a 32"–36" fiberglass tubing with a flexible shaft to extend over different bed sizes. The oxygen tubing is then threaded through the eye hooks on the shaft and the attached mask can fit any patient. The base of the unit is metal and is placed near the oxygen tank or air pump as used with a cardio pulmonary air pump assistance unit by the patient's bed and is eminently flexible in any direction.

10 Claims, 4 Drawing Sheets

TELESCOPING FLEXIBLE OXYGEN SUPPLY TUBE SUPPORT STAND

RELATED APPLICATIONS

The present invention was first described in Disclosure Document Number 457,928 filed on Apr. 21, 1999. There are no previously filed, nor currently any co-pending applications, anywhere in the world.

BACKGROUND OF THE INVENTION

1. Field of the Invention

The present invention relates generally to adjustable and retractable oxygen tube supply devices and, more particularly, to a telescoping, flexible, portable oxygen supply tube support stand.

2. Description of the Related Art

In an all too familiar hospital or extended care facility scene, the patient that requires oxygen or other similar gases, is often seen constantly fighting with the air tubing to keep it from becoming tangled or trapped when they move. Should the line become trapped under them or wrapped around an arm, the risk of the line becoming yanked away is great. Should the patient roll over while sleeping, the chances are even greater since they are not aware of it. If the mask becomes dislodged while sleeping, the patient is not afforded the medical benefits of the oxygen or gas. This may also present a constant worry to the patient, again resulting in a decrease of health. Accordingly, there is a need for a means by which air tubing used with patients on oxygen or other gases, can be kept from becoming tangled or trapped while in a bed. The development of the Telescoping Flexible Oxygen Tube Support Stand fulfills this need.

Within the related art, numerous applications exist for devices allowing patients to undergo oxygen therapy employing tubular recoil mechanisms for entanglement prevention. However, these devices limit the mobility of the patient who is connected wearing an oxygen mask connected to the oxygen tubing. Accordingly, there is a need for a means by for providing a patient wearing an oxygen mask much greater mobility, such as when rolling over in bed, while preventing the oxygen hose from becoming entangled.

In the related art, the following patents disclose a patient ventilating apparatus with a flexible tubular catheter. These include U.S. Pat. No. 5,645,048, issued in the name of Brodsky et al., and U.S. Pat. No. 5,355,876, issued in the name of Brodsky et al. U.S. Pat. No. 5,752,511, issued in the name of Simmons et al. describes an adjustable medical tube retainer and nasal dilator. U.S. Pat. No. 5,392,808, issued in the name of Pierce discloses a retractable tubing reel device for an oxygen supply tank. U.S. Pat. No. 4,739,757, issued in the name of Edwards describes a headband for supporting a nasal oxygen administering tube. U.S. Pat. No. 4,654,026, issued in the name of Underwood discloses an intravascular tube assembly with separators preventing entanglement. U.S. Pat. No. 4,593,688, issued in the name of Payton describes an adjustable and movable headpiece for providing a nebulized oxygen-enriched fog. U.S. Pat. No. 4,480,639, issued in the name of Peterson et al. discloses a medical tube restraining device.

Consequently, the development of present invention fulfills these cited needs in a manner not otherwise addressed in the art. A search of the prior art did not disclose any patents that read directly on the claims of the instant invention.

SUMMARY OF THE INVENTION

It is therefore an object of the present invention to provide an improved oxygen tube support stand that allows bed ridden patients receiving oxygen the ability to roll over and/or move without worrying about the oxygen tubing becoming entangled or trapped.

It is another object of the present invention to provide an improved oxygen tube support stand device that is adjustable for different sized bed and patients.

It is yet another object of the present invention to provide a flexible telescoping shaft that flexes and bends as the patient moves allowing the patient exceptional mobility.

It is an advantage of the present invention that it has multiple uses with either hospital beds, beds in the home, or nursing home beds.

It is another advantage of the present invention that it provides a portable weighted base preventing the present invention from tipping over and can be easily moved from one bed to another.

Briefly described according to the preferred embodiment of the present invention, the Telescoping Flexible Oxygen Tube Support Stand, as its name implies, is an apparatus to aid in the holding and retention of oxygen tubing used with patients in hospital beds. A large weighted base on the order of ten pounds is used as a counterweight on the floor next to the bed. A series of fiberglass rods extends up from the base to a height of approximately four to five feet. The rods form a structure that cantilevers over the center of the bed using a system of lockable angle adjusters. The tubing is then routed along these fiberglass rods from the oxygen tank or similar device. The tubing then hangs down from the end of the invention where the patient may utilize it through a mask or similar medical equipment. As the patient moves and rolls, the invention flexes and moves with the patient in a manner similar to that of a fishing pole. When the patient rolls back, the slack is taken up by the invention. The use of the Telescoping Flexible Oxygen Tube Support Stand allows patients on oxygen and who are confined to a bed, the ability to roll over and/or move without worrying about the oxygen tubing becoming entangled or trapped.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

| LIST OF REFERENCE NUMBERS | |
|---|---|
| 20 | Telescoping Flexible Oxygen Tube Support Stand |
| 30 | Weighted Base |
| 40 | Wheel Assembly |
| 50 | First Vertical Member |
| 50a | Sealing Ring |
| 60 | Second Vertical Member |
| 60a | Eyelet |
| 60b | Eyelet Aperture |
| 60c | Eyelet Inner Surface |
| 70 | Pivoting Means |
| 80 | Pivot Pin |
| 90 | Flexible Telescoping Shaft Assembly |
| 120 | First Arm |
| 120a | Eyelet |
| 120b | Eyelet Aperture |
| 120c | Eyelet Inner Surface |
| 130 | Second Arm |
| 140 | Third Arm |
| 150 | Oxygen Supply Tube |
| 160 | Supply Tuber Retaining Hook |
| 220 | Retaining Clips |

DESCRIPTION OF THE PREFERRED EMBODIMENTS

The best mode for carrying out the invention is presented in terms of its preferred embodiment, herein depicted within the Figures.

1. Detailed Description of the Figures

Figure 1:
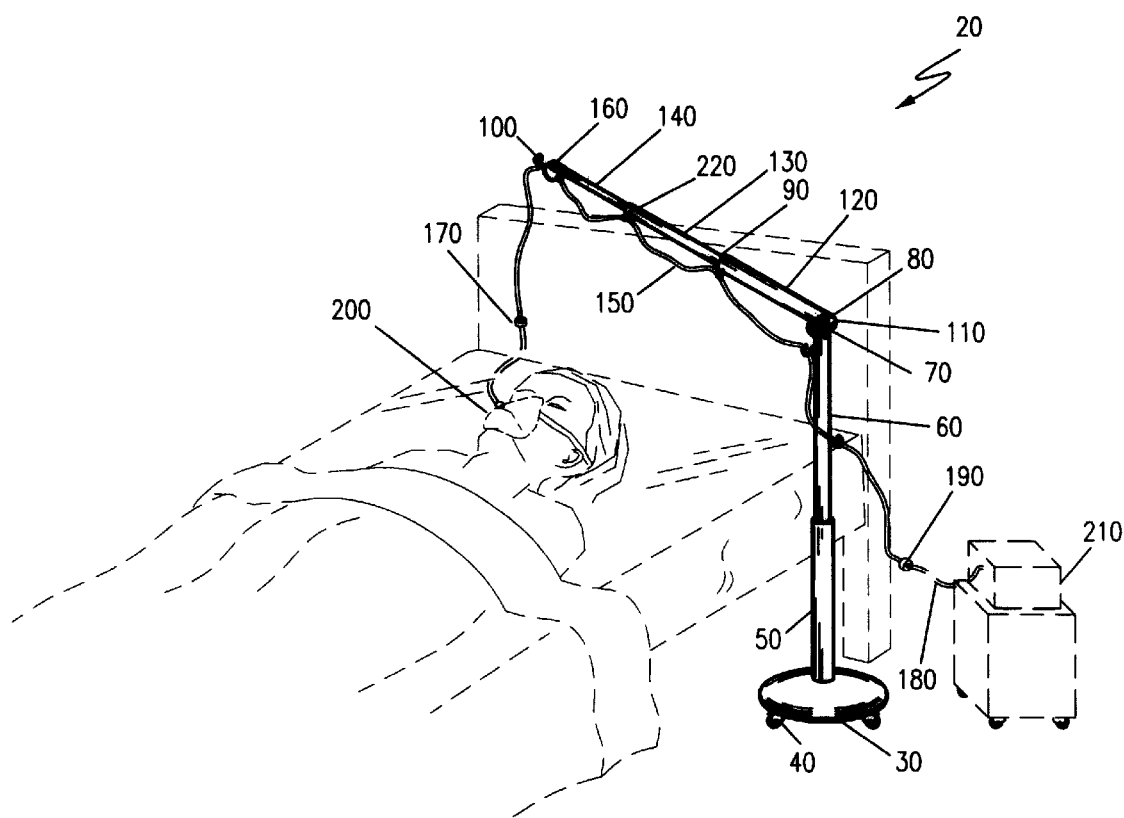
FIG. 1 is a perspective view of a Telescoping Flexible Oxygen Tube Support Stand in the extended configuration in use over a conventional bed, according to the preferred embodiment of the present invention.

Referring to FIG. 1, a Telescoping Flexible Oxygen Tube Support Stand is disclosed, comprised of a portable weighted base 30 of a generally disc-shaped configuration, and a plurality of wheel assemblies 40 mounted underneath to make the present invention readily movable. A first vertical member 50, having a first end and a second end, and of a generally linearly elongated tubular configuration, is mounted on the first end centrally on the upper surface of base 30 in a perpendicular fashion as shown. Many attachment means may be suitable to connect first vertical member 30 to base 30 as butt welding, bolting from beneath base 30 to a bracket mounted within first vertical member 30, or perhaps attaching a threaded adapter onto the first end of first vertical member 30 and forming a threaded aperture in the center of base 30 for specially receiving the adapter. For purposes of disclosure the means chosen is not significant.

The second end of first vertical member 50 is designed so as to receive a second vertical member 60 also of a generally linearly elongated tubular configuration and having a first end and a second end. The inner diameter of first vertical member 50 is slightly larger than the outer diameter of a second vertical member 60. The first end of second vertical member 60 is disposed within the first end of first vertical member 50 and communicates telescopingly therein in a semi-interference frictional arrangement. A sealing ring 50a is fitted over the joint between first vertical member 50 and second vertical member 60. First vertical member 50 and base 50 may be constructed from metal such as steel and then painted for aesthetic purposes. However, it is desirable that second vertical member 60 be constructed of some other material such as stainless steel since it will be continually exposed to surface abrasion and oxidation as it telescopes in and out of first member 50. A pivoting means 70 is joined at the second end of second vertical member 60. Pivoting means 70 is shown in greater detail in FIG. 3 and described further hereinbelow.

A flexible telescoping shaft assembly 90 is attached to pivoting means 70 at its anterior end 110 and extends outwardly terminating at a posterior end 100. The flexible telescoping shaft assembly 90 comprises a first arm 120, a second arm 130 and a third arm 140. First arm 120, attached at the anterior end 110 of flexible telescoping arm assembly 90, is of a generally linearly elongated tubular configuration of having an inner diameter capable of telescopingly receiving second arm 130. Second arm 130 is of a generally linearly elongated tubular configuration having an outer diameter capable of being telescopingly received by first arm 120. Third arm 140 is of a generally linearly elongated tubular configuration having an outer diameter capable of telescopingly being received within the inner diameter of second arm 130. First arm 120, second arm 130, and third arm 140 are manufactured from either carbon-fiber composites or fiberglass formed and cut into tubing of the appropriate inner and outer diameter. The material selected is essential to the proper functioning of the device as it must be capable of large inelastic deformations as the patient rolls over in bed. It is envisioned that carbon-fiber composites or fiberglass would have the required strength and flexibility but for purposes of disclosure, these are not the only materials that may be suitable.

As second arm 130 is extended or retracted, it frictionally engages the inner wall of first arm 120 and held into position thereby until such time as it is desired to again adjust the position of second arm 130. Likewise, as the third arm 130 is telescopingly extended, it frictionally engages the inner wall of second arm 130 and held into position thereby until such time as it is desired to again adjust the position of second arm 130. In this fashion, the flexible telescoping shaft 90 assembly can be extended for use or retracted for storage when not in use. Built in stops in both third arm 140 and second arm 130 would prevent third arm 140 from completely extending and exiting out of second arm 130, and likewise, to prevent second arm 130 from extending and exiting out of first arm 120.

Attached at the posterior end 100 of flexible telescoping shaft assembly 90 is an oxygen supply tube retaining hook 160. The supply tube retaining hook 160 is of a semi-spiral design whereby the oxygen supply tube 150 must be threaded around at least two spiral sections before entering a semi-enclosed section which bends in a ninety degree turn downward. In this fashion, the supply tube retaining hook 160 can receive and releasably hold an adequate length of a flexible, corrugated oxygen supply tube 150 (not part of the disclosure). One end of oxygen supply tube 150 is generally attached to an oxygen delivery apparatus 200 and an oxygen supply tank 210 (both of which are not part of the disclosure). Oxygen supply tube 150, which delivers oxygen to a patient from oxygen supply tank 210, is suspended with a plurality of retaining clips 220 which are staggered along the surface of telescoping shaft assembly 90 and second vertical member 60. Retaining clips 220 are of common design and may be attached via adhesive or screws. The other end of oxygen supply tube 150 is connected to an oxygen delivery mask strapped over the patients mouth while laying in bed.

Telescoping shaft assembly 90 is designed so as to bend effortlessly without undue restraints yet be of such strength so as to spring back to initial form. This design provides mobility to the patient and prevents oxygen supply tube 150 from constricting. It further allows a patient to safely move about in bed without fear of being entangled in oxygen supply tube 150 or constricting it and cutting off the source of vital rehabilitative oxygen.

Figure 2:
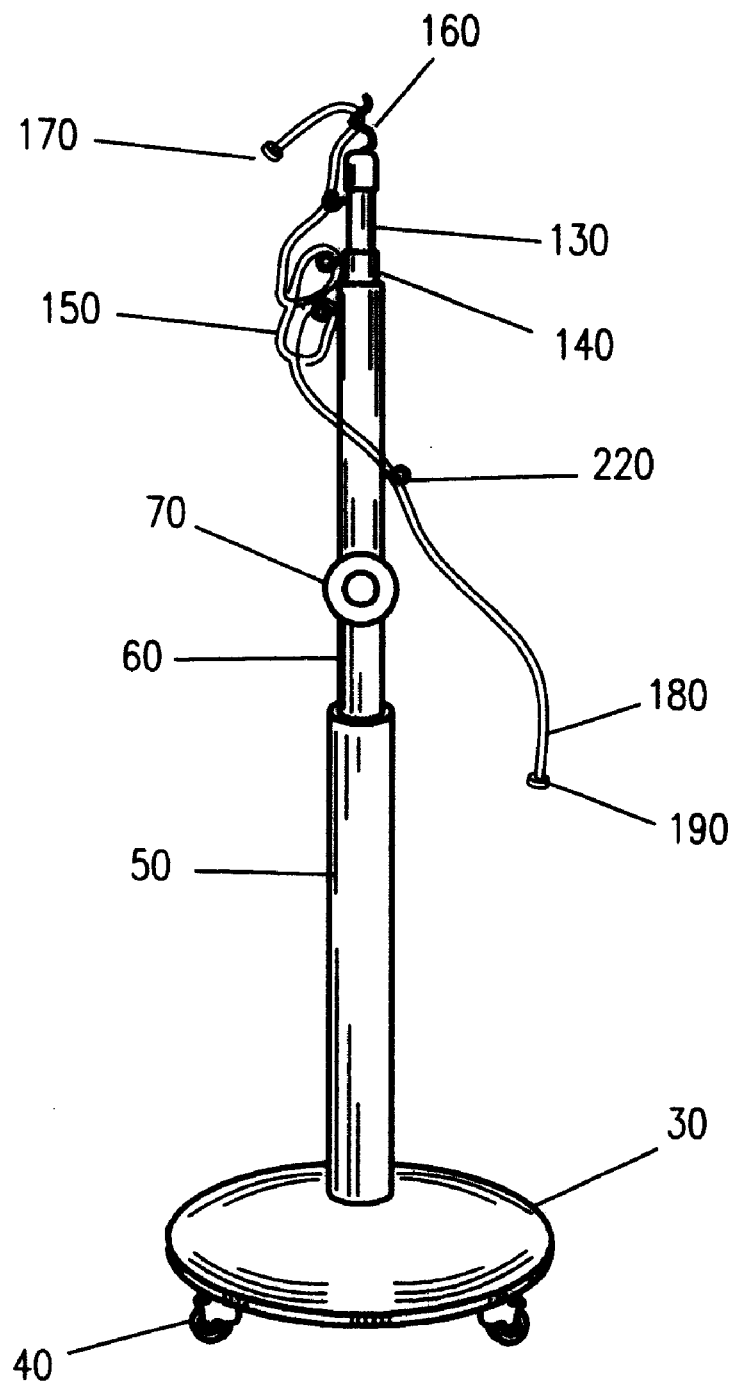
FIG. 2 is a front view of a Telescoping Flexible Oxygen Tube Support Stand in the retracted configuration, according to the preferred embodiment of the present invention.

Referring now to FIG. 2, Telescoping Flexible Oxygen Tube Support Stand 20 is shown in the retracted configuration wherein third arm 140 is completely retracted within second arm 130, and second arm 130 is completely retracted within first arm 120. First arm 120 may then be pivoted about pivoting means 80 so that it extends upwardly as shown for more compact storage. Typically, oxygen supply tube 150 may be disconnected from the oxygen source by a quick connect/disconnect connector so that it may remain attached to device 20 while it is storage. This enable the device 20 to be deployed rapidly when required. A wheel assembly 40 enables the device 20 to be easily moved about a level surface. Wheel assembly 40 consists of a plurality of four wheels attached to the bottom surface of base 30. Wheel assembly 40 may be equipped with locking wheels if so desired that would further inhibit the movement of device 20 unless it is desired to move it.

Figure 3:
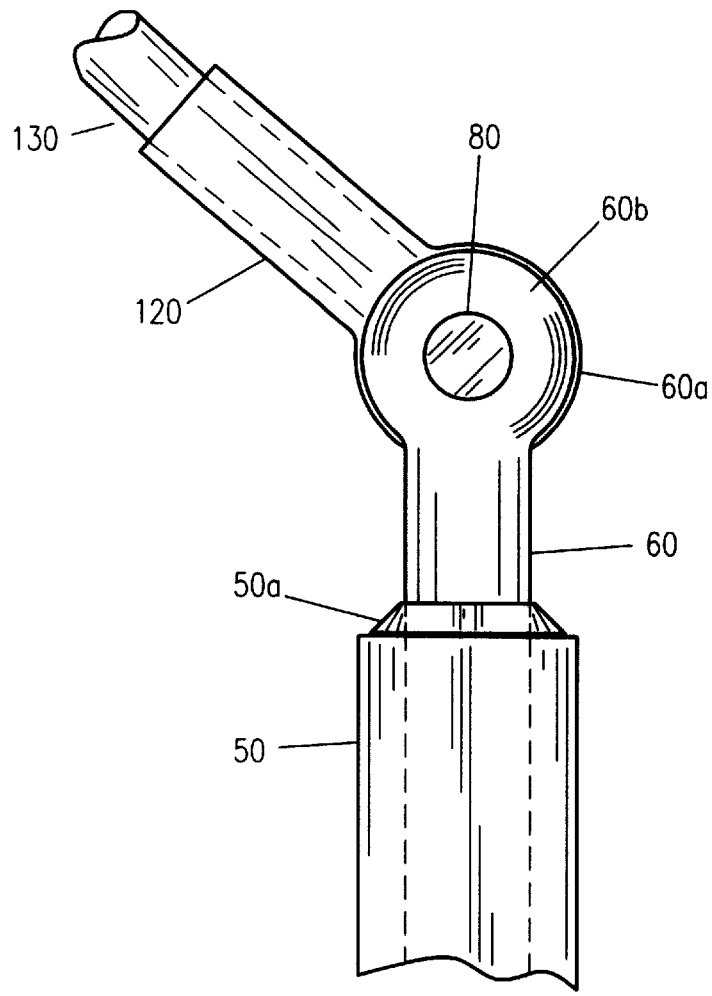
FIG. 3 is a partial cutaway front view of a telescoping shaft pivotally connected to a second vertical member of a Telescoping Flexible Oxygen Tube Support Stand, according to the preferred embodiment of the present invention.
Figure 3A:
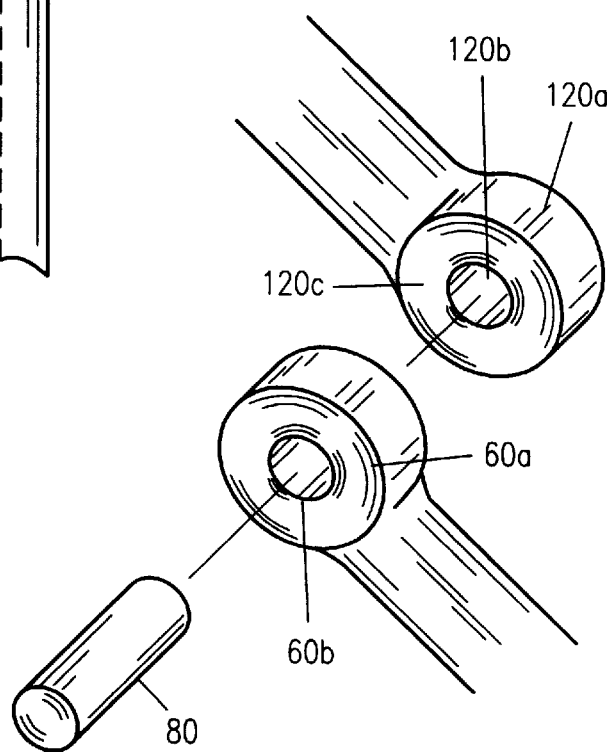
FIG. 3a is a partial cutaway perspective view of a the eyelet sections of a second vertical member, a first arm, and a pivot pin comprising a pivoting means for a Telescoping Flexible Oxygen Tube Support Stand, according to the preferred embodiment of the present invention.

FIG. 3 shows a partial cutaway view of pivoting means 80 pivotally connecting second vertical member 60 to first arm 120. For purposes of disclosure, pivoting means 80 is comprised of forming the ends of both second vertical member 60 and first arm 120 into eyelets 60a and 120a wherein the inward facing surfaces 60c and 120c, respectively, of eyelet 60a and 120a is smooth. The inwardly facing smooth surfaces 60c and 120c are designed to mate with each other and are pressed together so that a frictional force is developed when they are rotated relative to one another. Eyelet 60a and 120a of second vertical member 60 and first arm 120 are pressed together with pivot pin 70 which is pressed into an aperture 60b and 120b in the center of eyelet 60a and 120a, respectively. The composition of eyelet 60a and 120a are shown in greater detail in FIG. 3a.

Figure 4:
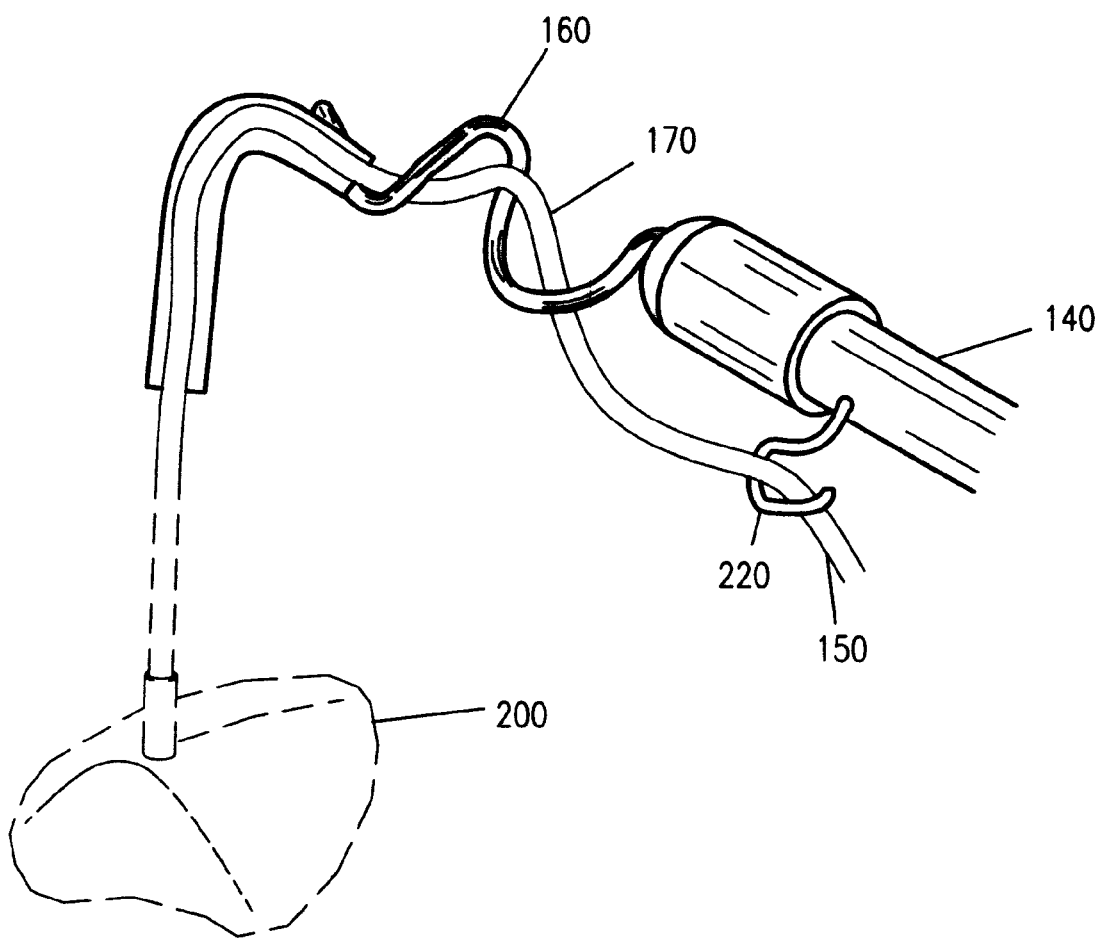
FIG. 4 is a partial cutaway perspective view of a free end of a telescoping shaft configured with a spiral-shaped and oxygen tube protector from a Telescoping Flexible Oxygen Tube Support Stand for receiving and supporting an oxygen delivery conduit, according to the preferred embodiment of the present invention.

Finally, in FIG. 4, shown is a partial cutaway view of the posterior end 100 of telescoping shaft assembly 90 showing supply tube retaining hook 160 supporting oxygen supply tube 15 in an overhead fashion and one of the plurality of eye hooks 220 for holding oxygen supply tube 220 snug against third arm 140.

2. Operation of the Preferred Embodiment

In operation, the present invention is rolled up against the bed of a patient either at home or in the hospital. An oxygen delivery tube is threaded through a series of retaining hooks located along the length of the vertical support shaft and the flexible telescoping shaft that extends over the bed. A hook at the end of the telescoping shaft supports the oxygen delivery tube in an overhead fashion. The end of the oxygen delivery tube is then connected to the patients oxygen mask. The other end of the tube is connected to a common medical oxygen supply. Both the height of the vertical support shaft and the length of the overhead telescoping shaft may be adjusted to give the occupant of the bed optimum slack in the oxygen supply tube. As the patient rolls over in bed, the flexible arms of the telescoping overhead shaft are designed to be flexible yet prevent the oxygen delivery tube from becoming entangled. When the device is no longer desired, the telescoping arms may be retracted and the device wheeled away.

The foregoing description is included to illustrate the operation of the preferred embodiment and is not meant to limit the scope of the invention. The scope of the invention is to be limited only by the following claims.

What is claimed is:

1. A telescoping, flexible, oxygen support stand for supporting a medical oxygen supply tube to a patient in an entanglement free manner, said stand comprised of:

a portable weighted base, said portable weighted base of a generally disc-shaped configuration;

a plurality of wheel assemblies, said plurality of wheel assemblies mounted underneath said portable weighted base;

a first vertical member, said first vertical member of a generally linearly elongated tubular configuration, and having a first end and a second end, and mounted on said first end centrally on an upper surface of said base in a perpendicular fashion;

a second vertical member, said second vertical member being of a generally linearly elongated tubular configuration, and having a first end and a second end, and wherein an inner diameter of said first vertical member is slightly larger than an outer diameter of said second vertical member so that the first end of said second vertical member may be disposed within said second end of said first vertical member and communicate telescopingly therein in a semi-interference frictional arrangement;

a sealing ring, said sealing ring fitted over a joint between said first vertical member and said second vertical member;

a pivoting means, said pivoting means joined at the second end of said second vertical member;

a flexible telescoping shaft assembly, said flexible telescoping shaft assembly having an anterior end and a posterior end and attached to said pivoting means at said anterior end and extending outwardly terminating at said posterior end; and an oxygen supply tube retaining hook, said oxygen supply tube retaining hook being of a semi-spiral design, and attached to said posterior end of said flexible telescoping shaft assembly, whereby said oxygen supply tube must be threaded around at least two spiral sections before entering a semi-enclosed section which bends in a ninety degree turn downward, and wherein said supply tube retaining hook can receive and releasably hold an adequate length of a flexible, corrugated oxygen supply tube in an entanglement free manner.

2. The telescoping, flexible, oxygen support stand of claim 1, wherein said flexible telescoping shaft assembly further comprises:

a first arm, said first arm attached at said posterior end of said flexible telescoping arm assembly and being of a generally linearly elongated tubular configuration;

a second arm, said second arm being of a generally linearly elongated tubular configuration having an outer diameter capable of being telescopingly received within the inner diameter of said first arm;

a third arm, said third arm being of a generally linearly elongated tubular configuration having an inner diameter capable of being telescopingly received within an inner diameter of said second arm; and wherein said first arm, said second arm, and said third arm are manufactured from a member of the group consisting of carbon-fiber composites or fiberglass formed and cut into tubing of the appropriate inner and outer diameter.

3. The telescoping, flexible, oxygen support stand of claim 2, wherein as second arm is extended or retracted, said second arm frictionally engages an inner wall of said first arm and held into position thereby until such time as it is desired to again adjust the position of said second arm, and likewise, as said third arm is telescopingly extended, said third arm frictionally engages an inner wall of said second arm and held into position thereby until such time as it is desired to again adjust the position of said second arm.

4. The telescoping, flexible, oxygen support stand of claim 3, wherein built in stops in both said third arm and said second arm prevent said third arm from completely extending and exiting out of said second arm, and likewise, to prevent said second arm from extending and exiting out of said first arm.

5. The telescoping, flexible, oxygen support stand of claim 4, wherein one end of said oxygen supply tube is generally attached to an oxygen delivery apparatus and an oxygen supply tank and the other end of said oxygen supply tube is connected to an oxygen delivery mask strapped over said patient's mouth while laying in a bed, whereby said oxygen supply tube is suspended with a plurality of retaining clips which are staggered along a surface of said telescoping shaft assembly and said second vertical member.

6. The telescoping, flexible, oxygen support stand of claim 5, wherein said retaining clips are of common design and may be attached with a member of the group comprised of adhesive or screws.

7. The telescoping, flexible, oxygen support stand of claim 6, wherein said telescoping shaft assembly is designed so as to bend effortlessly without undue restraints yet be of such strength so as to spring back to initial form, and further allows said patient mobility and prevents said oxygen supply tube from constricting while allowing said patient to safely move about in said bed without fear of being entangled in or constricting said oxygen supply tube.

8. The telescoping, flexible, oxygen support stand of claim 7, wherein said plurality of wheel assemblies enables said stand to be easily moved about a level surface, and is comprised of a plurality of four wheels attached said bottom surface of base and may be equipped with locking wheels that would further inhibit the movement of said stand unless it is desired to move said stand.

9. The telescoping, flexible, oxygen support stand of claim 8, wherein said pivoting means is comprised of forming the ends of both said second vertical member and said first arm into eyelets wherein the inward facing surfaces of said eyelets are smooth and designed to mate with each other, and further, when pressed together a frictional force is developed when said eyelets are rotated relative to one another.

10. The telescoping, flexible, oxygen support stand of claim 9, wherein said eyelets of said second vertical member and said first arm are pressed together with a pivot pin which is pressed into an aperture in the center of said eyelets.

* * * * *